United States Patent [19]

Narula

[11] Patent Number: 4,869,248
[45] Date of Patent: Sep. 26, 1989

[54] METHOD AND APPARATUS FOR LOCALIZED THERMAL ABLATION

[76] Inventor: Onkar S. Narula, 5765 SW. 117th St., Miami, Fla. 33156

[21] Appl. No.: 40,269

[22] Filed: Apr. 17, 1987

[51] Int. Cl.$^4$ ............................................. A61B 17/36
[52] U.S. Cl. ............................... 128/303.13; 128/784; 128/786
[58] Field of Search ............... 128/642, 784, 785, 786, 128/303.1, 419 D, 303.12, 303.13, 303.14, 303.15, 303.16, 303.17

[56] References Cited

U.S. PATENT DOCUMENTS

| | | | |
|---|---|---|---|
| 164,184 | 6/1875 | Kidden | 128/784 |
| 359,506 | 3/1887 | Goodwillie | 128/303.14 |
| 2,224,464 | 12/1940 | Wolf | 128/303.14 |
| 3,729,008 | 4/1973 | Berkovits | 128/418 |
| 3,886,944 | 6/1975 | Jamshidi | 178/303.1 |
| 3,915,174 | 10/1975 | Preston | 128/419 P |
| 3,935,857 | 2/1976 | Co | 128/2.05 |
| 4,169,464 | 10/1979 | Obrez | 128/657 |
| 4,394,866 | 7/1983 | Hughes | 128/785 |
| 4,402,328 | 9/1983 | Doring | 128/785 |
| 4,449,528 | 5/1984 | Auth et al. | 128/303.1 |
| 4,567,901 | 2/1986 | Harris | 128/786 |
| 4,641,649 | 2/1987 | Walinsky et al. | 128/303.1 |
| 4,643,187 | 2/1987 | Okada | 128/303.15 |
| 4,660,571 | 4/1987 | Hess et al. | 128/786 |
| 4,672,962 | 6/1987 | Hershenson | 128/303.1 |

FOREIGN PATENT DOCUMENTS

| | | | |
|---|---|---|---|
| 2952818 | 7/1981 | Fed. Rep. of Germany | 128/785 |
| 1140792 | 2/1985 | U.S.S.R. | 128/786 |

OTHER PUBLICATIONS

Onkar S. Narula et al., "Induction of AV Nodal (AVN) Delays and Block by a Thermal Catheter Technique: Acute and Chronic Studies", Abstracts, *JACC*, vol. 7, No. 2, Feb. 1986, p. 132A.
Onkar S. Narula et al., "Microtransection of the His Bundle With Laser Radiation Through a Pervenous Catheter: Correlation of Histologic and Electrophysiologic Data", *American Journal of Cardiology*, Jul. 1984, pp. 186–192.
R. Gonzalez et al., "Closed-Chest Electrode-Catheter Technique for His Bundle Ablation in Dogs", *Am. J. Physiol.* 241 (Heart Circ. Physiol. 10): H283–H287, 1981.
J. Gallagher et al., "Catheter Technique for Closed-Chest Ablation of the Atrioventricular Conduction System", *N. Engl. J. Med.*, vol. 306, No. 4, Jan. 28, 1982, pp. 194–200.
Geoffrey O. Hartzler, "Electrode Catheter Ablation of Refractory Focal Ventricular Tachycardia", *JACC*, vol. 2, No. 6, Dec. 1983: 1107–13, pp. 1107–1113.
Rolando Gonzalez et al., "Closed Chest Permanent Atrioventricular Block in Dogs", *American Heart Journal*, vol. 105, No. 3, Mar. 1983, pp. 461–470.

(List continued on next page.)

*Primary Examiner*—Max Hindenburg
*Assistant Examiner*—J. P. Lacyk
*Attorney, Agent, or Firm*—Wolf, Greenfield & Sacks

[57] ABSTRACT

A thermal ablation catheter for microtransection or macrotransection of conduction paths within the heart includes a resistive heating element at its distal end for highly localized treatment. The heating element includes a resistive wire loop connected to an external power source and has a prescribed shape to insure that the wire loop is approximately perpendicular to the surface to be treated. A reference electrode spaced 8–10 inches from the distal end is used in conjunction with the wire loop (the sensing electrode) to sense potentials in the heart. The catheter is advanced through a blood vessel to the region of the A-V node and the His bundle, and the sensing mode is used to determine the desired location for treatment. The wire loop is then energized with d.c. current for a predetermined time on the order of 2–5 seconds to cause localized thermal ablation of the target area.

27 Claims, 2 Drawing Sheets

OTHER PUBLICATIONS

Fred Morady et al., "Transvenous Catheter Ablation of a Posteroseptal Accessory Pathway in a Patient with the Wolff-Parkinson-White Syndrome", *The New England Journal of Medicine,* vol. 310, No. 11, Mar. 15, 1984, pp. 705–707.

Onkar S. Narula et al., "Laser Catheter-Induced Atrioventricular Nodal Delays and Atrioventricular Block in Dogs: Acute and Chronic Observations", *JACC,* vol. 5, No. 2, Feb. 1985: 259–67, pp. 259–267.

Garrett Lee, M.D. et al., "Effects of Laser Irradiation Delivered by Flexible Fiberoptic System on the Left Ventricular Internal Myocardium", *American Heart Journal,* vol. 106, No. 3, Sep. 1983, pp. 587–590.

Warren M. Jackman, M.D. et al., "Direct Endocardial Recording from an Accessory Atrioventricular Pathway: Localization of the Site of Block, Effect of Antiarrhythmic Drugs, and Attempt at Nonsurgical Ablation", *Circulation,* vol. 68, No. 5, Nov. 1983, pp. 906–916.

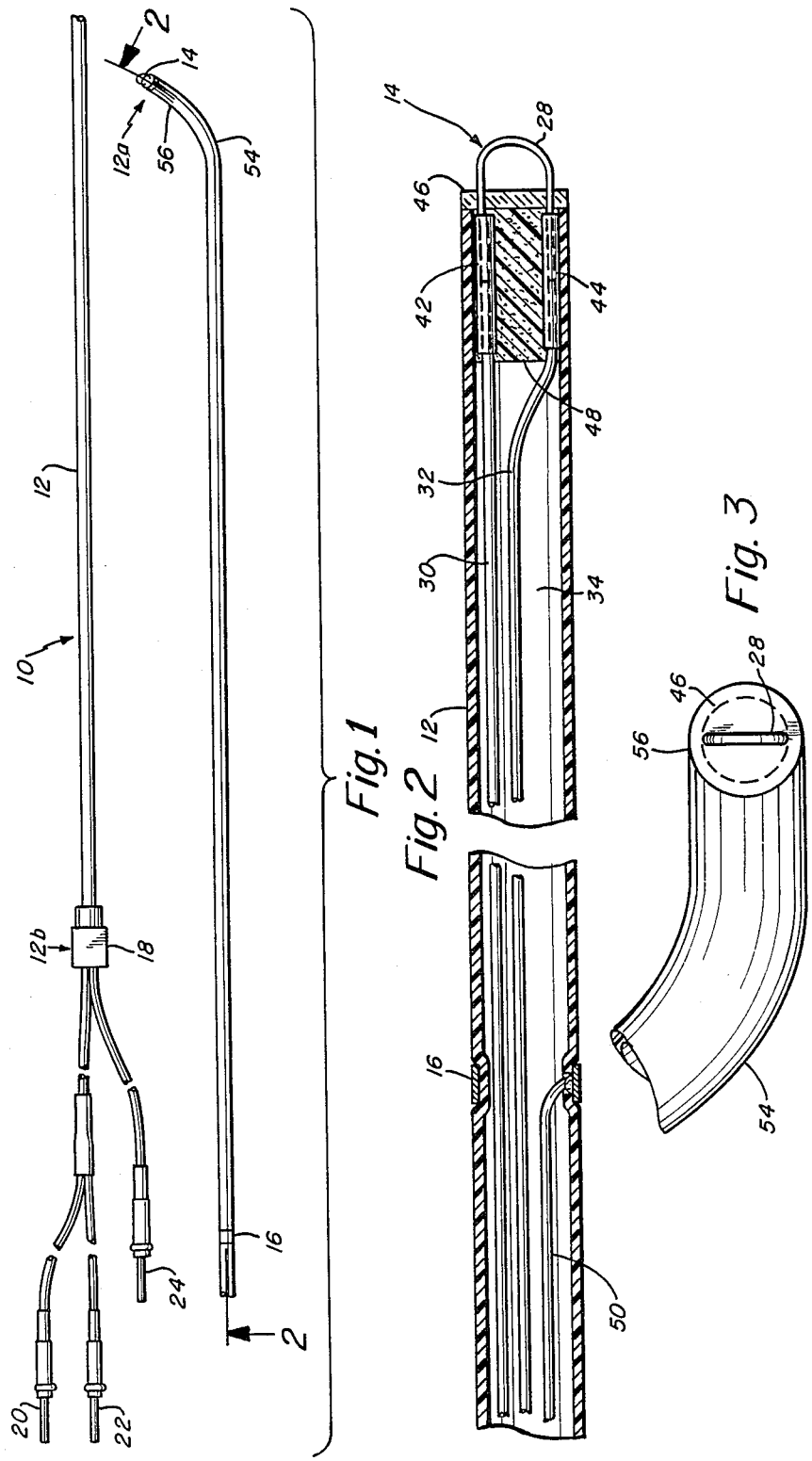

METHOD AND APPARATUS FOR LOCALIZED THERMAL ABLATION

FIELD OF THE INVENTION

This invention relates to a thermal ablation catheter and method of use and, more particularly, to a catheter having a resistive heating element at its distal end. The catheter is advanced through a blood vessel into the heart and is used for microtransection or macrotransection of conduction paths within the heart.

BACKGROUND OF THE INVENTION

In the treatment of various heart malfunctions, it has been found beneficial to modify the conduction paths within the heart, usually by cutting specific conduction paths, for example in the region of the A-V node or the His bundle or the ventricles. This can be accomplished surgically, but recently more preferable non-surgical techniques have been developed.

In one prior art technique, a catheter having one or more electrodes is advanced into the heart and a plate-like electrode is positioned external to the patient. A high energy d.c. voltage is applied between the electrodes causing a modification of the conduction system. Such a technique is described by J. Gallagher et al in "Catheter Technique for Closed-Chest Ablation of the Atrioventricular Conduction System," *New England Journal of Medicine*, Vol. 306, No. 4, Jan. 28, 1982, pp. 194–200. The d.c. shock technique causes burning of the tissue surrounding the electrode positioned in the heart and produces effects which are not at all localized.

A technique utilizing a laser catheter produces more localized effects. A catheter having an optical fiber passing through it is advanced to the desired location in the heart. Energy from an external laser is conducted by the optical fiber into the heart. This technique is described by Onkar S. Narula et al in "Microtransection of the His Bundle with Laser Radiation Through a Pervenous Catheter: Correlation of Histologic and Electrophysiologic Data," *American Journal of Cardiology*, July 1984, pp. 186–192. While the laser catheter technique produces localized effects, it requires complex and expensive equipment. In addition, a catheter containing an optical fiber has limited flexibility, thereby making it difficult to position the tip of the catheter in the desired location. Furthermore, a separate electrode and conductor must be provided for sensing potentials in the conduction paths. A technique for high frequency ablation of a His bundle in the heart is disclosed in U.S. Pat. No. 641,649, issued Feb. 10, 1987 to Walinsky et al. A catheter in the form of a coaxial transmission line with an antenna at its distal end is advanced into the heart in the region of the His bundle, and the potentials sensed by the catheter are measured and displayed. The catheter position is adjusted until the desired potentials are obtained. Then high frequency energy is applied to the transmission line causing ablation of portions of the His bundle. The high frequency technique produces undesirable burning of tissue surrounding the antenna, and its effects are not well localized.

A cauterizing electrode having a platinum wire loop at its tip is disclosed in U.S. Pat. No. 359,506 issued Mar. 15, 1887 to Goodwillie. Medical instruments having wire loops at their tips are also disclosed in U.S. Pat. No. 2,224,467 issued Dec. 10, 1940 to Wolf and in U.S. Pat. No. 4,643,187 issued Feb. 17, 1987 to Okada. None of these patents disclose a device which can be advanced through a blood vessel to the heart.

It is a general object of the present invention to provide methods and apparatus for non-surgical microtransection or macrotransection of desired portions of internal body organs.

It is another object of the present invention to provide methods and apparatus for localized microtransection or macrotransection of conduction paths within the heart.

It is a further object of the present invention to provide a thin, flexible catheter which can be advanced through a body vessel to perform localized thermal ablation of internal body organs.

It is still another object of the present invention to provide methods and apparatus for sensing conduction potentials within the heart and for performing localized thermal ablation of the conduction paths.

It is still another object of the present invention to provide a thin, flexible catheter having a resistive heating element at its distal end to perform localized thermal ablation.

It is a still further object of the present invention to provide a thin, flexible catheter having a prescribed shape so that a resistive heating element at the distal end contacts a desired location in a prescribed alignment therewith.

SUMMARY OF THE INVENTION

According to the present invention, these and other objects and advantages are achieved in a thin, flexible catheter which can be advanced through a body vessel to an internal organ for microtransection or macrotransection of a desired portion of the internal organ. The catheter comprises an elongated thin, flexible tube having a distal end and a proximal end, a resistive heating element at the distal end of the flexible tube and coupling means for coupling the resistive heating element to a source of electrical energy. The heating element causes localized thermal ablation of the desired portion of the organ when energized. Preferably, the catheter has a suitable diameter and flexibility for passage through a blood vessel to the heart.

In a preferred embodiment, the heating element comprises a prescribed length of resistive heating wire formed into a loop at the distal end of the flexible tube and the coupling means comprises a pair of electrical conductors connected to opposite ends of the heating wire and passing through the flexible tube to the proximal end thereof. The size and shape of the heating element can be selected in accordance with the procedure to be performed. The flexible catheter can further be provided with means for positioning the heating element in a prescribed alignment with the surface to be treated. The positioning means preferably comprises the distal end of the catheter having a predetermined shape based on the relative orientations of the body vessel through which the catheter passes and the part of the internal organ to be treated. The heating element also functions as a sensing electrode and is used to map the target site.

The catheter can further include a reference electrode proximally spaced from the heating element and an electrical conductor connected to the reference electrode and passing through the catheter to the proximal end thereof.

In a preferred method of use, the catheter is advanced through a blood vessel to a desired location in the heart, and the potentials between the heating element and the reference electrode are observed. The heating element can be moved until the desired potentials are observed. The heating element is then energized causing localized thermal ablation of a desired portion of the heart. Potentials are again observed to determine the effect of the thermal ablation. The procedure can be repeated as necessary.

The catheter is connected to an external power source including means for supplying electrical power through the electrical conductors to the heating element for a predetermined time interval. The power source can be a d.c. source.

According to another aspect of the present invention, there is provided a method for microtransection or macrotransection of a conduction path in the heart comprising the steps of providing a thin, flexible catheter having a resistive heating element at its distal end, advancing the flexible catheter through a blood vessel to the heart, placing the heating element in contact with a conduction path to be treated, and supplying electrical energy to the heating element for a predetermined time interval sufficient to cause localized thermal ablation of the conduction path.

BRIEF DESCRIPTION OF THE DRAWINGS

For a better understanding of the present invention, together with other and further objects, advantages and capabilities thereof, reference is made to the accompanying drawing which are incorporated herein by reference and in which:

FIG. 1 is an elevation view of a catheter in accordance with the present invention;

FIG. 2 is an enlarged cross-section of the distal end of the catheter taken along line 2—2 of FIG. 1;

FIG. 3 is an elevation view of the distal end of the catheter; and

DETAILED DESCRIPTION OF THE INVENTION

Figure 4:
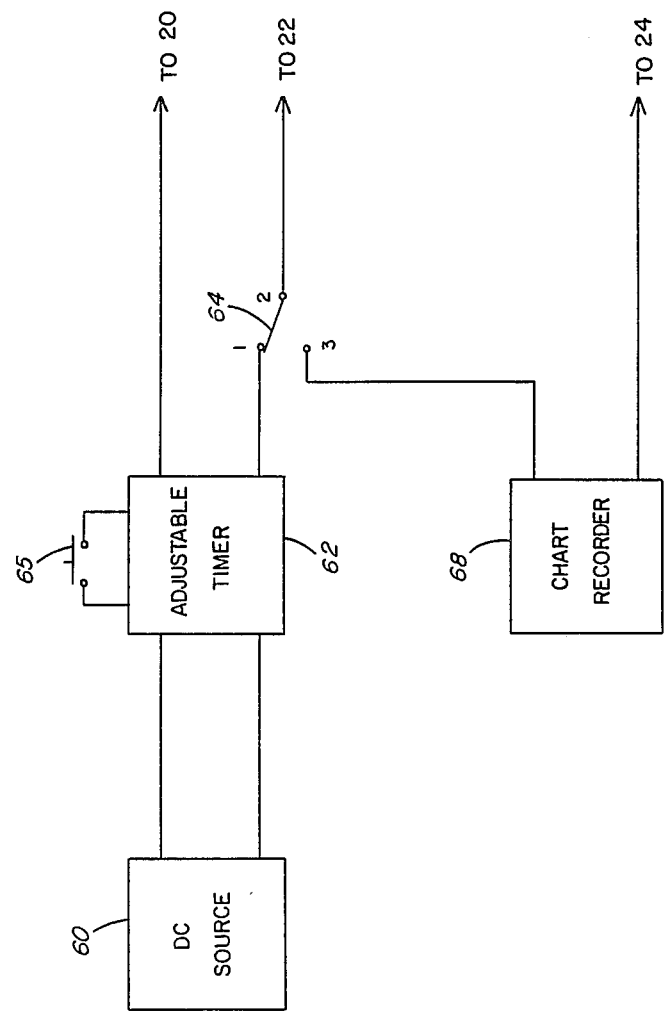
FIG. 4 is a block diagram showing a power source and sensing device for use with the catheter in FIG. 1.

A catheter for performing localized thermal ablation in accordance with the present invention is shown in FIG. 1. The catheter includes an elongated, thin flexible tube 12 having a distal end 12a and a proximal end 12b. The distal end 12a is provided with a resistive heating element 14 and is optionally provided with a predetermined shape as described hereinafter. The heating element 14 also functions as a sensing electrode to record local electrical potentials from the target site and is used for mapping. Optional additional sensing electrodes may be placed at different sites along the shaft of the catheter. The electrode 16 is proximally spaced from the distal end 12a and acts as a ground or reference electrode. The proximal end 12b is provided with a bushing 18 and three electrical connectors 20, 22, 24. Connection of either of the connectors 20, 22 to a sensing recorder provide unipolar recording of electrical potentials when used with reference electrode 16. The catheter may contain an additional lumen traversing through its length and exiting at the distal end for purposes of fluid, drug administration or recording of intracardiac pressures.

A preferred application of the thermal ablation catheter shown in FIG. 1 and described herein is for microtransection or macrotransection of conduction paths within the heart. In particular, the catheter is used for modification of the A-V node, peri A-V nodal region, and the His bundle. The catheter can be used to interrupt or modify other electrical pathways in the heart. The catheter 10 is introduced through a vessel and is advanced to the heart. Due to the small size of the resistive heating element 14, very localized ablation of the desired segment of the conduction system can be accomplished. The catheter 10 has sufficient flexibility and is sufficiently small in diameter so that it can be passed through a blood vessel to the heart.

A cross-sectional view of the distal end 12a of catheter 10 is shown in FIG. 2. The heating element 14 includes a resistive wire loop 28 connected at opposite ends to electrical conductors 30, 32. The electrical conductors 30, 32 pass through a central lumen 34 in the flexible tube 12 to the proximal end thereof and are coupled to connectors 20, 22, respectively. When the connectors 20, 22 are coupled to a suitable source of electrical energy, the heating element 14 rapidly increases in temperature due to resistive heating. In general, the heating element 14 of the present invention can comprise any resistively heated element of suitable size for passing through a body vessel to the organ to be treated. Thus, the invention is not limited to use of a wire loop. The wire loop 28 is also used as a sensing electrode when either of the connectors 20 or 22 are used in conjunction with the reference electrode 16. This enables mapping of electrical potentials and localization of the target site before and after ablation.

The wire loop 28 can have any convenient shape. Preferably, it has a semicircular shape with straight end portions for connection to conductors 30, 32. Alternatively, the wire loop 28 can comprise between a half-circle and a full circle (for example, a 270° portion of a circle) with straight end portions for connection to conductors 30, 32. The size and shape of the wire loop 28 can be selected in accordance with the procedure to be performed. Catheters have been constructed in accordance with the present invention wherein the wire loop 28 has an inside diameter d of 0.050-inch, 0.065-inch and 0.072-inch.

The wire loop 28 can be formed of any rugged, resistive material. One suitable material is Elgiloy, which is a registered trademark of the Elgiloy Company. Elgiloy is an alloy of cobalt, chromium and nickel. Another suitable material is nickel-chromium wire. Wire having a diameter in the range between about 0.006-inch and 0.008-inch is suitable to provide the desired heating. The wire loop 28 in a preferred embodiment has a resistance of about 500–600 ohms. It will be understood by those skilled in the art that various wire materials, resistivities and diameters can be employed within the scope of the present invention.

The conductors 30, 32 can be any relatively flexible insulated conductor. They must have sufficiently low resistance to limit the voltage drop through the catheter 10 when current is supplied to wire loop 28. In a preferred embodiment, each of the conductors 30, 32 includes two 31-gauge copper wires, individually insulated with polyurethane. Two wires were used for each conductor to limit the voltage drop through the catheter. The conductors 30, 32 were welded to opposite ends of the wire loop 28 and then were mechanically secured with crimp connections 42, 44. It will be understood that any suitable technique for connecting conductors 30, 32 to wire loop 28 can be utilized.

The flexible tube 12 can comprise any conventional catheter tube of suitable flexibility, torque control and diameter. In a preferred embodiment, a 7 French catheter (0.091-inch maximum diameter) was utilized.

The wire loop 28 is supported by an insulating disk, or collar, 46 attached to the end of the flexible tube 12 and having holes therethrough for passage of the ends of the wire loop 28. The collar 46 maintains the wire loop 28 in a fixed position relative to the flexible tube 12 and also insulates the distal end of tube 12 from the heat produced by the wire loop 28 when it is in operation. Preferably, the crimp connections 42, 44 between the wire loop 28 and conductors 30, 32 are made as close to collar 46 as possible in order to limit the generation of heat proximally of the collar 46. Such heat could cause melting and damage of the distal end of flexible tube 12.

The collar 46 can be fabricated from any suitable temperature-resistant insulator. One preferred material is Macor, a machinable glass ceramic produced by Corning Glass. Anodized aluminum can also be utilized. The collar 46 and the crimp connections 42, 44 can be secured in position at the end of flexible tube 12 by epoxy 48. The collar 46 can be constructed with a shoulder which extends into the tip of tube 12 and, optionally, can be provided with an extension for spacing crimp connections 42, 44 apart.

The reference electrode 16 is proximally spaced about 8–10 inches back from the distal end 12a of the catheter 10. The reference electrode 16 can comprise a cylindrical metal sleeve coaxial with the flexible tube 12. In a preferred embodiment, the proximal electrode 16 is platinum. A conductor 50 is connected to reference electrode 16 and passes through lumen 34 to the proximal end of the catheter where it is coupled to connector 24. In an alternate embodiment, a wire braid is incorporated in the wall of the flexible tube 12, and the wire braid is electrically connected to reference electrode 16 using silver-filled conductive epoxy.

When the connectors 20, 22 are connected to a source of electrical energy, electrical current passes through the wire loop 28 causing a rapid increase in temperature. By proper selection of the resistance of wire loop 28 and the voltage applied to it, the wire loop 28 in less than one second reaches a temperature sufficient to cause thermal ablation of tissue. In a preferred embodiment, the loop 28 has a resistance of about 500 ohms and 10 volts d.c. are, applied to it. The size and shape of the wire loop 28 can be selected for effective treatment of the target area, with the limitation that the loop must be sufficiently small to easily pass through a blood vessel or other body vessel.

It is desirable that the distal end of the catheter 10 including the heating element 14 have a prescribed orientation relative to the surface to be treated in order to efficiently perform thermal ablation with the heating element 14. For A-V node and His bundle ablation, the preferred orientation is approximately perpendicular to the endocardial surface. If the distal end of the catheter 10 were to lay parallel or nearly parallel to the surface to be treated, good contact between the heating element 14 and the area to be treated could not be insured. Accordingly, the distal portion of catheter 10 is preferably preformed into a predetermined shape in order to insure a prescribed alignment between the distal end 12a and the surface to be treated. The shape is based on the relative orientations of the body vessel through which the catheter passes and the surface area to be treated. It will be understood that the shape of the catheter and the orientation relative to the surface to be treated depend on the particular application, and that shaping of the catheter is not necessary for all applications.

In the case where the catheter is used for partial or complete thermal ablation of the A-V node or the His bundle and the catheter is advanced into the heart through the femoral vein, a double curvature is preferred. The preferred shape has a first gentle curve or bend 54 spaced by a first distance from the distal end 12a and a second gentle curve or bend 56 spaced by a second distance from the distal end 12a. The distance to the first bend 54 is greater than the distance to the second bend 56. In a preferred embodiment, the distance between the first bend 54 and the distal end is about 3 cm, and the distance between the second bend 56 and the distal end is about 1 cm. The first bend 54 is toward a first direction generally orthogonal to the longitudinal axis of the catheter and the second bend 56 is toward a second direction generally orthogonal to both the axis of the catheter and the first direction. Described another way, if the catheter 10 is oriented vertically, the first bend 54 is toward a left-to-right direction, and the second bend 56 is toward a front-to-rear direction. It will be understood that the distance between bends is variable depending on the size of the heart. According to another feature of the invention, the catheter 10 may be provided with a very gentle curve over a distance of 10–15 cm in a proximal direction from the first bend 54 in order to further assist in properly positioning the heating element 14 relative to the A-V node and the His bundle in the heart. The preferred shape can be imparted to the catheter 10 by heating the distal end of flexible tube 12 in a mold. The polymer material of the tube 12 retains the shape after cooling.

The external portion of the thermal ablation system is shown in block diagram form in FIG. 4. A d.c. source 60 has its output coupled to an adjustable timer 62. In a preferred embodiment, the d.c. source 60 is a 10 volt nickel cadmium battery. One output of the adjustable timer 62 is coupled to connector 20 of the catheter 10 and the other output of adjustable timer 62 is coupled to terminal 1 of a switch 64. Common terminal 2 of the switch 64 is coupled to connector 22 of catheter 10. A switch 65 is connected to adjustable timer 62 for initiating an output to the catheter 10. When switch 65 is closed and switch 64 is in position 1, the adjustable timer 62 connects the d.c. source 60 to connectors 20, 22 for a predetermined time interval in the range between 0.1 and 10 seconds. A chart recorder 68 has one input lead connected to terminal 3 of switch 64 and the other input lead connected to connector 24 of catheter 10. When switch 64 is switched to position 3, the chart recorder 68 records the potential between the wire loop 28 and the reference electrode 16 of the catheter 10. Switch 64 determines the mode of operation of the catheter 10. Position 1 is the thermal ablation mode, and position 3 is the sensing mode.

It will be understood by those skilled in the art that the voltage of the source 60 and the resistance of the wire loop 28 can have any compatible values suitable for producing the desired thermal output. In addition, the time interval during which power is applied to the heating element can have any suitable duration to accomplish the desired thermal ablation and is not limited to the range between 0.1 and 10 seconds. Furthermore, the battery used in source 60 can be replaced with an a.c. to d.c. power supply having suitable ground protection. The power source can be provided with meters for monitoring the battery voltage, the catheter voltage and catheter current, and a current adjustment for limiting the currents supplied to the catheter. An alarm or other indicator can be provided when an open circuit is sensed in wire loop 28. Adjustable current limiting of the output to the wire loop 28 is also desirable.

In operation, the catheter 10 is advanced through a blood vessel to the approximate desired location in the heart. The sensing mode is enabled by placing switch 64 in position 3 and the potentials between wire loop 28 and the sensing electrode 16 are monitored by chart recorder 68. The sensing mode is utilized to locate the exact location for thermal ablation. When the desired location has been determined by interpretation of the sensed potentials, switch 64 is placed in position 1 and the wire loop 28 is energized for a selected time duration on the order of 2–5 seconds by closing switch 65. Heat generated by the wire loop 28 causes a localized thermal ablation or microtransection of the conduction path. Then, the sensing mode is again enabled in order to determine the effect of the microtransection procedure. The process can be repeated as many times a necessary to obtain satisfactory results. The sensing function effectively permits mapping of the potentials in the targeted area.

The catheter of the present invention for providing localized thermal ablation can also be utilized for a variety of other applications including management of coronary artery disease, for elimination of obstruction in the coronary arteries, and for coronary angioplasty. The technique is likely to be useful in valvuloplasty of stenotic aortic, tricuspid, pulmonic, and even mitral valves and should be preferable over balloon valvuloplasty as the opening of the stenotic valve can be controlled precisely.

The present invention offers several advantages over the current method of DC shock. These are as follows:

1. Patients do not require general anesthesia as the procedure of the invention can be performed without sedation. Only local anesthesia is used to anesthetize the femoral area at the point of insertion of the catheters. Patients experience no sensation at the time of delivery of energy. This is in complete contrast to the pain associated with delivery of d.c. shock.

2. The procedure of the invention requires delivery of only minimal amounts of energy in the range of 6–12 Joules which is less than 1/100 as compared to 400–1800 Joules of energy required with d.c. shock.

3. With the procedure of the invention, only a small area targeted for modification is affected and tissue injury is limited to 1–2 mm by 2–3 mm as compared to injury over 1 cm by 2 cm noted during d.c. shock.

4. Most important of all is that with the procedure of the invention, 1:1 A-V conduction is retained and complete heart block is not induced in contrast to production of complete A-V block and implantation of a permanent pacemaker with d.c. shock ablation.

5. Since the procedure of the invention utilizes only very small amounts of energy, the complications associated with delivery of high amounts of energy noted with d.c. shock therapy should not occur. With d.c. shock therapy, complications such as perforation of the heart, death, coronary arterial thrombosis, thrombus of the coronary sinus, ventricular arrhythmia or new ectopic arrhythmias have been documented. In addition, the published data documents that the success rate with d.c. shock ablation is no more than 65–70% and even in those patients in whom the procedure is successful, the arrhythmias recur and A-V conduction resumes. Some of these patients require second and third procedures. Although our data is from a limited number of patients, the conduction changes accomplished in all of these patients have persisted without any progression or regression. This data is also supported by our canine experimental data which documented no progression or regression of conduction delays.

While there has been shown and described what is at present considered the preferred embodiments of the present invention, it will be obvious to those skilled in the art that various changes and modifications may be made therein without departing from the scope of the invention as defined by the appended claims.

I claim:

1. A thin, flexible catheter which can be advanced through a body vessel to an internal organ for microtransection or macrotransection of a desired portion of the internal organ, said catheter comprising:
   an elongated, thin flexible tube having a distal end and a proximal end;
   a resistive heating element attached to said flexible tube;
   coupling means for coupling said resistive heating element to a source of electrical energy in an ablation mode to cause resistive heating of said heating element, said heating element thereby producing localized thermal ablation of the desired portion of the organ when energized; and
   a reference electrode attached to said flexible tube and proximally spaced from said heating element, said heating element and said reference electrode functioning in a sensing mode as sensing electrodes.

2. A flexible catheter as defined in claim 1 wherein said flexible tube has a diameter and flexibility selected to facilitate passage through a blood vessel to the heart.

3. A flexible catheter as defined in claim 2 wherein said heating element comprises a prescribed length of resistive heating wire.

4. A flexible catheter as defined in claim 3 wherein said heating wire is formed into a loop at the distal end of said flexible tube.

5. A flexible catheter as defined in claim 4 wherein said coupling means comprises a pair of electrical conductors connected to opposite ends of said heating wire and passing through said flexible tube to the proximal end thereof.

6. A flexible catheter as defined in claim 4 wherein said loop is supported at the distal end of said flexible tube by an insulating collar attached to the distal end thereof.

7. A flexible catheter as defined in claim 2 further including means for positioning said heating element in a prescribed alignment with a surface to be treated.

8. A flexible catheter as defined in claim 7 wherein said positioning means comprises a portion of said flexible tube near the distal end thereof having a predetermined shape based on the relative orientations of the body vessel through which the catheter passes and the surface to be treated.

9. A flexible catheter as defined in claim 8 wherein said catheter includes a longitudinal axis and wherein said predetermined shape includes a first relatively gentle bend spaced by a first distance from said distal end and a second relatively gentle bend spaced by a second distance from said distal end, said first distance being greater than said second distance, said first bend being toward a first direction generally orthogonal to the longitudinal axis of the catheter and said second bend being toward a second direction generally orthogonal to both said axis and said first direction.

10. A flexible catheter as defined in claim 1 wherein said reference electrode is proximally spaced in the range between about 8 and 10 inches from said heating element.

11. A flexible catheter as defined in claim 10 wherein said reference electrode comprises a cylindrical sleeve coaxial with said flexible tube.

12. A thin, flexible catheter for passage through a blood vessel to the heart and for microtransection or macrotransection of a localized portion of the heart, said catheter comprising:

an elongated, thin flexible tube having a distal end and a proximal end, a resistive heating element at the distal end of said flexible tube, said heating element including a prescribed length of resistive heating wire formed into a loop that is exposed for direct contact with the localized portion of the heart;

mean for coupling said heating element to a source of electrical energy including a pair of electrical conductors connected to opposite ends of said heating wire and passing through said flexible tube to the proximal end of said flexible tube, said loop being raised to a sufficient temperature when energized by said source to effect localized thermal ablation of the localized portion of the heart, and a reference electrode attached to said flexible tube and proximally spaced from said heating element, and an electrical conductor connected to said reference electrode and passing through said flexible tube.

13. A flexible catheter as defined in claim 12 wherein said loop is supported at the distal end of said flexible tube by an insulating collar attached to the distal end thereof.

14. A flexible catheter as defined in claim 12 wherein a portion of said flexible tube near the distal end thereof is provided with a predetermined shape for positioning said heating element in a prescribed alignment with a surface to be treated.

15. A flexible catheter as defined in claim 14 wherein said catheter includes a longitudinal axis and wherein said predetermined shape includes a first relatively gentle bend spaced by a first distance from said distal end and a second relatively gentle bend spaced by a second distance from said distal end, said first bend being greater than said second distance, said first bend being toward a first direction generally orthogonal to the longitudinal axis of the catheter and said second bend being toward a second direction generally orthogonal to both said axis and said first direction.

16. A flexible catheter as defined in claim 12 wherein said loop includes a semicircular portion having a diameter of about 1-2 millimeters.

17. A flexible catheter as defined in claim 16 wherein said heating wire has a diameter in the range between about 0.006 inch and 0.008 inch.

18. Apparatus for microtransection of a desired portion of an internal body organ comprising:

a thin, flexible catheter for passage through a body vessel to the internal organ including an elongated, thin flexible tube having a distal end and a proximal end;

a resistive heating element at the distal end of said flexible tube, said heating element including a prescribed length of resistive heating wire, and a pair of electrical conductors connected to opposite ends of said heating wire and passing through said flexible tube;

electrical power source means including means for supplying electrical power through said electrical conductors to said heating element for a predetermined time interval, said heating element causing localized thermal ablation of the desired portion of the organ when energized; and means for sensing electrical potentials within the heart to assist in determining a suitable location for thermal ablation and to evaluate the effect of thermal ablation, said sensing means including a reference electrode attached to said flexible tube and proximally spaced from said heating element, a third electrical conductor connected to said reference electrode and passing through said flexible tube, and means coupled to said third electrical conductor and at least one of said pair of conductors connected to said heating element for recording the potential between said heating element and said reference electrode.

19. Apparatus as defined in claim 18 wherein said flexible catheter has a diameter and flexibility selected to facilitate passage through a blood vessel to the heart.

20. Apparatus as defined in claim 19 wherein said power source means includes a d.c. source for supplying d.c. current to said heating element for said predetermined time interval.

21. Apparatus as defined in claim 20 wherein said power source means further includes timer means for supplying d.c. current to said heating element for a time in the range between 0.1 and 10 seconds.

22. A method for microtransection or macrotransection of a conduction path in the heart comprising the steps of:

providing a thin, flexible catheter having a resistive heating element at its distal end;

advancing the flexible catheter through a blood vessel to the heart;

placing the heating element in contact with the conduction path to be treated; and supplying electrical energy to said heating element for a predetermined time interval sufficient to cause localized thermal ablation of said conduction path.

23. A method as defined in claim 22 wherein the step of placing the heating element in contact with the conduction path to be treated includes the steps of:

sensing electrical potentials within the heart from the heating element at the distal end, and moving the heating element within the heart until a desired electrical potential is sensed.

24. A method as defined in claim 22 wherein the step of placing the heating element in contact with the conduction path to be treated includes the step of placing the heating element in a prescribed alignment with the conduction path to be treated.

25. A method as defined in claim 22 wherein the step of providing a thin, flexible catheter includes the step of selecting the size and shape of the heating element for effective treatment of the conduction path.

26. A thin, flexible catheter which can be advanced through a blood vessel to the heart for microtransection or macrotransection of a localized portion of the heart, said catheter comprising:

an elongated, flexible catheter lead having a distal end and a proximal end;

a resistive heating element at the distal end of said catheter lead;

a reference electrode attached to said catheter lead and proximally spaced from said heating element;

means for coupling said heating element to a source of electrical energy for thermal ablation of the localized portion of the heart in an ablation mode; and means for sensing an electrical potential between said heating element and said reference electrode in a sensing mode.

27. A catheter as defined in claim 26 wherein said heating element includes a resistive heating wire formed into a loop that is exposed for direct contact with localized portion of the heart.

* * * * *